United States Patent [19]

Arena et al.

[11] Patent Number: 4,970,302

[45] Date of Patent: Nov. 13, 1990

[54] SELECTIVE CATALYTIC CONVERSION OF CYANOHYDRINS TO THEIR CORRESPONDING ALDEHYDES WITHOUT CONCURRENT AMINE FORMATION

[75] Inventors: Blaise J. Arena, Des Plaines; Paul R. Kurek, Barrington, both of Ill.

[73] Assignee: Allied-Signal Inc., Morris Township, Morris County, N.J.

[21] Appl. No.: 344,181

[22] Filed: Apr. 27, 1989

[51] Int. Cl.$^5$ .................. C07H 1/00; C07H 5/00; C07C 255/00
[52] U.S. Cl. .................. 536/124; 536/17.9; 536/17.2; 536/22; 536/55.2; 536/55.3; 502/102
[58] Field of Search ............ 536/124, 4.1, 17.9, 536/19.2, 22, 55.2, 55.3; 526/905; 502/100, 102

[56] References Cited

U.S. PATENT DOCUMENTS

| | | | |
|---|---|---|---|
| 4,581,447 | 4/1986 | Arena | 536/125 |
| 4,717,696 | 1/1988 | Arena | 536/124 |

OTHER PUBLICATIONS

H. S. Isbell and H. L. Frush, *J. Org. Chem.*, 23, 1309 (1958).

*Primary Examiner*—Ronald W. Griffin
*Assistant Examiner*—Everett White
*Attorney, Agent, or Firm*—Eugene I. Snyder; Harold N. Wells; Gerard P. Rooney

[57] ABSTRACT

There is described a method of selectively and continuously converting a cyanohydrin to its corresponding aldehyde using as a catalyst zerovalent palladium dispersed on an organic polymeric resin with a surface area above 30 m$^2$/g under highly acidic conditions where the formed imine is resistant to further reduction to the amine. Where the aqueous cyanohydrin feedstock contains more than 1.4 equivalent proportions of a strong acid, less than 5% of the theoretical yield of amine is formed. Hydrogenation may be performed at a pressure as great as 2000 psig without significant deleterious effects on selectivity. Hydrolysis of the hydrogenation product affords the corresponding aldehydes in good yields.

17 Claims, 1 Drawing Sheet

SELECTIVE CATALYTIC CONVERSION OF CYANOHYDRINS TO THEIR CORRESPONDING ALDEHYDES WITHOUT CONCURRENT AMINE FORMATION

One of several synthetic procedures available for one-carbon homologation of monosaccharides is the addition of the elements of HCN to aldehydes to afford, generally, an epimeric pair of cyanohydrins, with subsequent reduction of the nitrile group of the latter under conditions where the formed imine is concurrently hydrolyzed to its corresponding aldose, as shown by the equation,

Recently we have shown in U.S. Pat. No. 4,581,447 that this approach provides an effective entry into the family of L-sugars, although several aspects of the synthesis required new developments before commercial feasibility became a reality.

The transformation of the intermediate cyanohydrin to its corresponding aldehyde is a curious one involving two consecutive reactions and requiring quite high discrimination among several reaction pathways. What is required is the reduction of the nitrile group to an imine followed by rapid hydrolysis of the imine to its corresponding aldehyde with minimal hydrogenation of the imine to its amine and of the aldehyde to its alcohol.

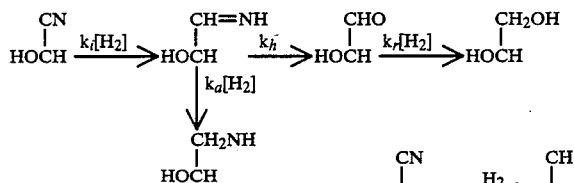

In the context of competing reactions the requirements for selectivity are that $k_i >> k_a$, $k_h >> k_a[H_2]$, and assuming that hydrogenation of the nitrile is the rate limiting step in the above sequence, that $k_r << k_i$. These requirements place a heavy burden on the catalyst used in selective hydrogenation-hydrolysis of cyanohydrins, but even these requirements are augmented by the need for the catalyst to be active at relatively low reaction temperatures (since the cyanohydrins are not particularly thermostable), by the need for the catalyst to be relatively resistant to poisoning by nitrogen-containing organic materials, and by the need for the catalyst to be hydrothermally stable at the low pH required for this transformation.

Previously these needs and requirements have been met, virtually uniquely, by a catalyst of zerovalent palladium supported on barium sulfate. As a zerovalent metal active at low temperatures in the reduction of nitriles, palladium is relatively resistant to poisoning by organic nitrogen-containing compounds, especially amines. By working in a restricted pH range and under hydrogen-poor conditions it was possible to favor hydrolysis of the imine to the aldehyde, and to limit amine formation via reduction of the imine. By performing the reaction over a limited temperature range it was possible to minimize the decomposition of reactants so as to give a process yielding the desired product aldehyde at commercially acceptable levels; see U.S. Pat. No. 4,581,447. More recently we have described catalysts which, compared to palladium on barium sulfate, are both more resistant to poisoning and more selective in hydrogenation. Although this development led to a further reduction in amine formation, amines remained a significant byproduct. Total elimination of amine formation remained a high priority whose accomplishment eluded us.

During the course of an investigation into the hydrogenation of a mixture of glucocyanohydrin and mannocyanohydrin we experienced poor product balance under certain reaction conditions. Although reactant cyanohydrins were being consumed, inadequate glucose and mannose was produced based on the amount of cyanohydrin which disappeared. Further investigation demonstrated that glucose and mannose was formed in the reaction mixture long after hydrogenation was completed, as if the reaction mixture contained a stable precursor which reacted slowly to give glucose and mannose. After further investigation the following was postulated as the relevant reaction path.

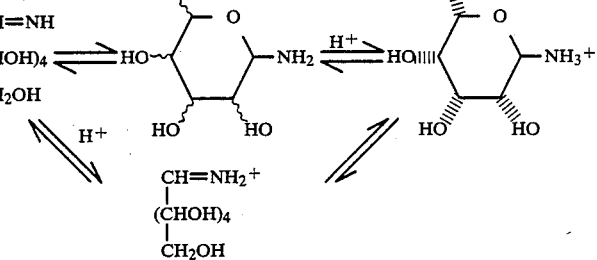

What attached special importance to the foregoing was the observation that under conditions where glucose and mannose were formed long after hydrogenation had ceased, virtually no amine was formed; amine product formation had for all practical purposes been eliminated.

The sequence above predicts that if hydrogenation is performed under sufficiently acidic conditions, all of the formed imine would be "trapped" as the protonated pyranosyl amine, and no glucose or mannose would be formed during hydrogenation. Indeed, subsequent experiments verified this prediction. But what was particularly striking was the absence of amine produced during hydrogenation which implied that the pyranosyl amine was quite resistant to further hydrogenation. Recalling that a hexose such as glucose can be readily reduced because of the equilibrium between the pyranose and open chain form, it could be expected that equilibrium between the pyranose and the open chain form of the imine, whether or not protonated, also would lead to amine via reduction of the imine. This is not the case, and whatever may be its reason the virtual elimination of amine as a hydrogenation product certainly is unprecedented. In his study of the mutarotation, hydrolysis, and rearrangement reactions of glycosylamines Isbell and coworkers noted that glycosylamine hydrolysis rates were very low in strongly acidic solutions, and postulated that the presence of a general base was necessary for hydrolysis via the open chain immonium ion. See H. S. Isbell and H. L. Frush, J. Org. Chem., 23, 1309 (1958) and references cited therein. However stable the protonated pyranosyl (or furanosyl) amine may be at low pH, it is not clear how this is related, if at all, to the equilibrium between these ring forms and the open chain immonium ion.

Our observation also led to a method of selectively converting cyanohydrins to aldehydes with more than 95 percent exclusion of amine as a concurrent reaction product. The process which is our invention reduces cyanohydrins under conditions of high acidity where the intermediate imine is unreactive both as to further hydrogenation and as to hydrolysis. After hydrogenation of the cyanohydrin is complete, the reaction mixture is separated from both the hydrogenation catalyst and hydrogen. When acid is removed from the reaction mixture the imine hydrolyzes to the corresponding aldehyde which is then recovered as the desired product of one-carbon homologation of monosaccharides.

SUMMARY OF THE INVENTION

The purpose of our invention is to selectively convert cyanohydrins which are the HCN adducts of aldotetroses, aldopentoses, and aldohexoses to their corresponding aldehydes with high selectivity and with the virtual elimination of amine as the byproduct. An embodiment is the hydrogenation of aqueous solutions of cyanohydrins under sufficiently acidic conditions to stabilize the formed imine, separating the aqueous solution of the imine, and hydrolyzing it in the absence of hydrogen to its aldehyde(s). In a more specific embodiment the aqueous solution contains at least 1.4 equivalents of a strong acid relative to the cyanohydrin. In a still more specific embodiment the aqueous solution which is hydrogenated contains at least about 8 weight percent sulfuric acid.

DESCRIPTION OF THE INVENTION

Figure 1:
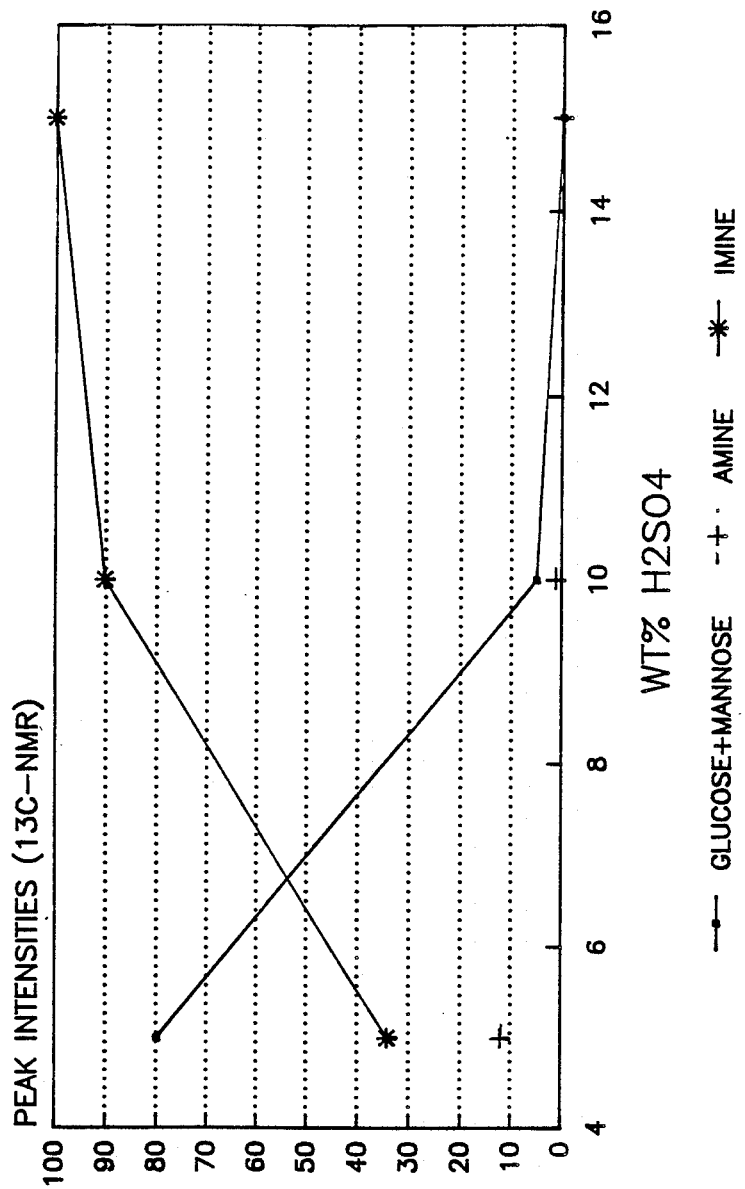
FIG. 1 shows the dependence of glucose plus mannose, imine, and amine concentration on sulfuric acid concentration in hydrogenation at 23° C., 600 psig $H_2$.

Our invention utilizes a method of selectively hydrogenating cyanohydrins under highly acidic conditions where the resultant imine is stable to both further hydrogenation and to hydrolysis. In our method the intermediate imine, postulated to be stabilized in its protonated pyranose form, is isolated as an aqueous solution and subsequently hydrolyzed in the absence of hydrogen by removal of acid. The result is the formation of aldehydes with largely complete elimination of amine, formed by reduction of the imine, as a byproduct. More specifically, amine is formed in less than about 5 percent theoretical yield. Previously, the selectivity of the conversion of cyanohydrins to their aldehydes by hydrogenation-hydrolysis was quite sensitive to hydrogen pressure, and because selective hydrogenation required hydrogen-poor conditions the prior art methods suffered from low conversion rates. A further benefit accruing from the present method is a greatly reduced sensitivity of the selectivity to reaction conditions, especially hydrogen pressure. In particular, since formation of a stabilized imine and its intrinsic stability is a function largely of acid concentration, hydrogenation can be performed at a much higher pressure than taught in the prior art without adversely affecting the selectivity of cyanohydrin conversion. Another incidental benefit is the elimination of alcohol formation via reduction of the product aldehyde, since in the present method aldehyde is formed in the absence of hydrogen.

Our invention is applicable to cyanohydrins which are the adducts of an aldose and hydrogen cyanide, HCN. Of particular importance are the tetroses, pentoses, and hexoses. Erythrose and threose exemplify the tetroses, while ribose, arabinose, xylose and lyxose exemplify the pentoses. Examples of a hexose include allose, altrose, glucose, mannose, gulose, idose, galactose, and talose. As can be readily appreciated, our process is equally applicable to the D-series of aldoses and the L-series. The cyanohydrins are used as aqueous solutions whose concentration is desirably as high as possible to maximize productivity. In the most usual case the feedstock will contain from about 5 through about 25 weight percent of cyanohydrin. Concentrations as high as 50 weight percent may be feasible; concentrations under 5 weight percent may be used, but generally with lower productivity.

The acidity of the aqueous solution of cyanohydrin used as a feedstock is a key to the success of our invention. In particular, it has been found that for imine stabilization under reaction conditions there is required a strong acid in an amount sufficient to afford at least 1.4 equivalents of acid per mole of cyanohydrin being reduced. By "strong acid" is meant an acid which is considered completely, or virtually completely, dissociated. Examples of strong acids which may be used in our invention include sulfuric acid, phosphoric acid, hydrochloric acid, and trifluoroacetic acid, with sulfuric acid being preferred solely for reasons of convenience. Using sulfuric acid as an example, the requirement of having at least 1.4 equivalents of acid per mole of cyanohydrin requires 0.7 moles of sulfuric acid per mole of cyanohydrin, since sulfuric acid is a diprotic mineral acid. Although there does not appear to be an upper limit to the amount of acid which may be used, when more than about 3 equivalents of acid is used per mole of cyanohydrin there is little, if any, incremental benefit. As a practical matter then, our invention may be practiced within the range from about 1.4 to about 3 equivalents of acid per mole of cyanohydrin. To give a concrete example, using a common stock solution containing 22 weight percent of a mixture of glucocyanohydrin and mannocyanohydrin, a mixture of 92 parts by weight of this stock solution with 8 parts by weight of sulfuric acid affords 1.4 equivalents sulfuric acid per mole of cyanohydrin; using 84.6 parts by weight of the stock solution and 15.4 parts by weight of sulfuric acid affords an aqueous feedstock containing 3 equivalents of sulfuric acid per mole of cyanohydrin mixture.

Since acid concentration is the key to selectivity, the nature of hydrogenation catalysts which may be used in the practice of this invention is less important than in other processes for analogous cyanohydrin conversions. However, since such catalysts are employed in highly acidic aqueous solutions it is apparent that they must be stable under these reaction conditions. The most useful class of catalysts is that of supported zerovalent palladium. Although the classic catalyst of palladium and barium sulfate may be used, a preferred catalyst is that of zerovalent palladium dispersed on a polymeric organic resin having a surface area of at least 30 m$^2$/g. The palladium is zerovalent and is neither in a higher oxidation state nor complexed with other ligands. The organic resin on which it is dispersed serves only as a relatively porous physical structure on which zerovalent palladium is more or less uniformly dispersed, but the resin must be stable under the highly acidic conditions under which hydrogenation is performed. Examples of resins which may be successfully used in the practice of this invention include polystyrene, polyacrylamide, and poly(vinylpyridine). Resins bearing strongly acidic functional groups seem to be desirable and may be exemplified by divinylbenzene-crosslinked polystyrene having pendant sulfonic acid groups (available under the trade name XN1010 from Rohm & Haas) and polystyrene having pendant perfluoroalkyl carboxylic acid groups as exemplified by NAFION resins from E. I. DuPont. Among the preferred resins are polystyrenes, especially the polystyrenes with pendant perfluoroalkyl carboxylic acid groups, and polyacrylamides. Resins having a surface area greater than about 50 m$^2$/g are preferred, and those with a surface area over about 100 m$^2$/g are even more highly preferred.

The hydrogenation of cyanohydrins to the stabilized imine is effected by contacting the acidic aqueous solution of the cyanohydrin with a supported zerovalent palladium catalyst and hydrogen at a pressure up to about 2,000 pounds per square inch and at a temperature from 10 to about 85° C. Although the prior art has necessarily used low hydrogen pressures to effect selective hydrogenation of cyanohydrins, one benefit of our invention is that the selectivity of cyanohydrin hydrogenation is essentially independent of hydrogen pressure, at least up to about 2,000 pounds per square inch. Our invention permits hydrogenation at a much higher pressure than was formerly possible without adversely affecting selectivity and with a substantially higher rate of conversion. Hydrogen pressures between about 100 and about 1500 pounds per square inch are most often used for convenience with the range from 600 to 1000 psig most frequently employed, but it needs to be emphasized that hydrogen pressure is no longer the critical factor as was the case with prior art methods.

Hydrogenation is effected in a range between about 10° and about 85° C., although at temperatures in excess of about 50° C. the cyanohydrins frequently are less stable and undesirable byproducts accompany the major ones. It is for this reason that temperatures are usually held at no more than about 50° C., with reductions usually being carried out in a temperature range between about 20° and about 45° C. But it needs to be recognized that where all reactants and products are stable at temperatures over 50° C. then higher temperatures may be employed without detriment.

When hydrogenation of this cyanohydrin feedstock is complete, the aqueous solution of the resulting stabilized imine product is separated from hydrogen. In practice, hydrogen is vented, replaced first by an inert gas, and catalyst is separated from the aqueous product mixture, as by filtration. However, in principle, subsequent hydrolysis of the imine may not require removal of the catalyst so long as hydrolysis is conducted in the absence of hydrogen. But we emphasize that for practical purposes the stabilized aqueous imine solution is separated both from the hydrogenation catalyst and hydrogen prior to imine hydrolysis.

The stabilized imine in solution is then hydrolyzed by removal of acid. Any method which effects removal of acid can be successfully employed to hydrolyze the imine. Such methods include electrodialysis, neutralization of acid to a pH greater than about 3, precipitation of imine with concurrent hydrolysis of the precipitate, and thermal hydrolysis. For example, removal of salts via electrodialysis effectively drives to completion the hydrolysis of imines to aldehydes. As another example, the hydrolytic liability of imines leads to their rapid hydrolysis at ambient temperature at a pH above about 3. Consequently partial neutralization of the strong acid suffices for complete hydrolysis. It also has been observed that at temperatures above 85° C., and especially above 95° C., the protonated imines hydrolyze even in highly acidic solutions. Consequently the hydrogenation reaction mixture may be simply heated for a short period, typically about 3 hours at 100° C., to effect imine hydrolysis. Finally, the imine salt precipitated from highly acidic aqueous solutions, as with ethanol, undergoes very rapid hydrolysis upon addition of water or exposure to the moisture in air.

The following examples will serve to illustrate this invention and are intended only as representative illustrations of its successful practice. These examples should not be interpreted as limiting our invention in any way, and variants which will be recognized by the skilled worker are intended to be encompassed within our invention.

EXAMPLE 1

Preparation of Standard Cyanohydrin Feedstock. To an Erlenmeyer flask was charged 200 g (0.24 moles) of a 22 weight percent aqueous solution containing a mixture of gluco- and mannocyanohydrins. The flask was cooled in a dry ice bath at −78° C. and to it was slowly added 35.6 g 98 weight percent (cold) H$_2$SO$_4$ (0.36 moles) in 2–3 g portions accompanied by vigorous shaking to mix the contents. After all of the acid was added, the mixture was allowed to reach 23° C. prior to hydrogenation.

Typical Hydrogenation Procedure. To a 100 cc glass liner for use in an 850 cc rotating bomb was charged 20 g feed (15 weight percent acid stabilized) and 0.5 g of a catalyst containing 4 weight percent zerovalent palladium on a washed polystyrene support (XAD-4 from Rohm and Haas). The bomb was flushed with nitrogen then charged to 500–1000 psig with hydrogen. Hydrogenation proceeded at 35° C. for 3–10 hours. The bomb was cooled, vented and flushed with nitrogen and the reaction mixture was filtered through Whatman #41 filter paper to remove catalyst. The filtrate was analyzed by ion chromatography (IC), $^{13}$C NMR and HPLC for sugars, cyanohydrins, acids, amides and lactones.

EXAMPLE 2

Effect of Acid Concentration and Pressure on Hydrogenation. Aqueous solutions of a mixture of mannocyanohydrin and glucocyanohydrin feedstock (21-2 weight percent cyanohydrin) containing variable amounts of sulfuric acid were hydrogenated in a rotating autoclave at differing pressures at 23° C. using as a catalyst 2.5 weight percent of a composite having 4 weight percent zerovalent palladium dispersed on XAD-4 resin (see Example 1). Results are summarized below in Tables 1 and 2 and in FIG. 1.

TABLE 1

Effect of Pressure and Acid Concentration on Cyanohydrin Hydrogenation

| Run[c] | Acid weight percent | Acid relative equivalents[a] | Hydrogen Pressure, psig | Cyanohydrin[b] | Glucose/Mannose[b] | Imine[b] | Amine[b] |
|---|---|---|---|---|---|---|---|
| 1 | 5 | 0.9 | 600 | 0 | 80 | 34 | 12 |
| 2 | 10 | 1.8 | 600 | 1 | 5 | 90 | 1 |
| 3 | 15 | 2.9 | 600 | 0 | 0 | 100 | 0 |
| 4 | 8 | 1.4 | 60 | 0 | 0 | 100 | 0 |
| 5 | 8 | 1.4 | 200 | 5 | 5 | 97 | 1 |
| 6 | 8 | 1.4 | 1000 | 0 | 0 | 100 | 3 |

[a]Number of equivalents acid per equivalent cyanohydrin in feed.
[b]All analysis were performed by $^{13}$C-NMR. Numbers refer to relative intensities of the C-1 signal normalized relative to the imine peak in run 4 which was arbitrarily assigned a value of 100.
[c]Hydrogenation time: runs 1–3, 7 hours; runs 4–6, 3 hours.

TABLE 2

Effect of Sulfuric Acid Concentration on Imine Stability in Cyanohydrin Hydrogenation (600 psig, 23° C.)

| Run | Weight % Acid | Weight Percent[a] Glucose | Cyano. | Mannose | Peak Areas by $^{13}$C-NMR[b] Amine | Imine | Mannose/Glucose |
|---|---|---|---|---|---|---|---|
| 1 | 0[c] | 0.49 | 3.9 | 0.06 | 0 | 8 | 0 |
| 2 | 5 | 1.7 | 6.5 | 5.8 | 12 | 34 | 80 |
| 3 | 10 | 0.34 | 3.3 | 1.4 | 1 | 90 | 5 |
|   |    | (5.1)[c] | (2.5)[c] | (8.7)[c] | 0.5[c] | 0[c] | 100[c] |
| 4 | 15 | 0.16 | 2.5 | 0.88 | 0 | 100 | 0 |

[a]By ion chromatography
[b]See footnote b, Table 1
[c]After hydrolysis of mixture by partial neutralization to pH 4.

These results show that imine is stabilized at acid concentrations affording 1.4 equivalents acid per equivalent cyanohydrin with virtually no amine formed during hydrogenation. The data also point to imine (as its salt) as virtually the sole product at pressures of 60–1000 psig; i.e., catalyst selectivity is independent of pressure at high acid concentrations.

EXAMPLE 3

Effect of Specific Acids on Hydrogenation. Using the feedstock and hydrogenation catalyst of Example 2, hydrogenations were performed at 35° C., 60 psig, for 3 hours in the presence of 15 weight percent of different acids with the results given in Table 3. It is clear from the data that best results are obtained using sulfuric acid.

TABLE 3

Stabilization of Imines During Hydrogenation

| Acid | Weight Percent (ion chromatography) Glucose | Cyanohydrin | Mannose | Peak Areas by $^{13}$C-NMR[a] Amine | Imine | Glucose + Mannose |
|---|---|---|---|---|---|---|
| $H_2SO_4$ | 0.2 | 0.3 | 0.7 | 0 | 98 | 0 |
| $H_3PO_4$ | 0.8 | 0.4 | 2.7 | 3 | 42 | 33 |
| HAc | 2.2 | 0.3 | 6.1 | 23 | 86 | 23 |

[a]See footnote b, Table 1.

EXAMPLE 4

Hydrolysis of Imine by Electrodialysis. Twenty-five grams of 22 wt. % stabilized glucose/mannose imine solution containing 15 weight percent sulfuric acid was diluted with 35 g of water. The conductivity of this solution was 190 ms/cm. This solution was fed into an electrodialysis unit and treated over the course of 5 hours. After 2.5 hours an additional 10 g of water was added to compensate for losses. When the solution conductivity reached 22 ms/cm the waste salt stream was replaced with fresh water in order to drive the electrodialysis to lower conductivity. The procedure continued until the conductivity of the product (imine containing) solution reached 0.2 ms/cm at the end of 5 hours of total treatment time.

The solution recovered contained upon analysis by HPLC 1.37 g of L-glucose and 4.62 g of L-mannose. No imine was detected by $^{13}$C-NMR; during the electrodialysis procedure all of the imine had been hydrolyzed to L-glucose, L-mannose.

Thermal Hydrolysis of Imines. To a rotating autoclave glass liner was charged 10 g of a filtered, catalyst free imine feedstock. The liner was charged to a rotating autoclave and was flushed with nitrogen. It was then pressured to 1000 psig with nitrogen and the contents heated at temperature (35° C. > 100° C. range) for 3 hours.

Hydrolysis of Imine by Precipitation in Ethanol. Two g of a filtered imine solution resulting from hydrogenation of a standard cyanohydrin feedstock (21.4 weight percent imine) was added dropwise to 10 g of cold ethanol at 10° C. A total of 0.73 g (96 weight percent) of precipitate was collected (0.43 g imine and 0.3 g reaction salts) by filtration and washed with cold ethanol. When distilled water was added to the precipitate the imine dissolved and hydrolyzed. The imine is hydroscopic and will undergo spontaneous hydrolysis.

Hydrolysis of Imine by pH Adjustment with Base. 10 g of a filtered imine solution resulting from hydrogenation of a standard cyanohydrin feed (~20-24 weight percent imine) was charged to an Erlenmeyer flask placed in an ice bath at 0° to 10° C. A stock solution of sodium hydroxide (10-20 weight percent) was prepared and also cooled. The sodium hydroxide solution was slowly added dropwise with stirring to the Erlenmeyer to give a solution with pH=4-5. The solution turned to a slight clear yellow tint and sodium chloride precipitated. The NaCl can be filtered off to afford a solution of the resulting glucose/mannose mixture.

EXAMPLE 5

Continuous Fixed Bed Hydrogenation of Cyanohydrin. Nineteen grams of a catalyst composed of 4% zerovalent palladium on polystyrene (XAD-4 from Rhom & Haas, surface area 725 $m^2/g$) may be used as a fixed bed for the hydrogenation of a feedstock containing 24 weight per cent aqueous epimeric cyanohydrins. To the feedstock, previously adjusted to pH 2.0, may be added sulfuric acid to a ratio of 2.9:1 equivalents. The reactor may be run at 1000 psig hydrogen at a bed temperature of 30° C., and feed flow rate of 10 cc/hr in an upflow mode. Cyanohydrin conversion of 90% may be obtained with 75% selectivity to the imine with little aldose or amine product formed.

What is claimed is:

1. A process for selectively converting a cyanohydrin which is the HCN adduct of an aldotetrose, aldopentose, or aldohexose to its corresponding aldehyde accompanied by less than about 5 percent theoretical yield of amine comprising contacting an aqueous solution of a cyanohydrin, said aqueous solution containing acid in an amount sufficient to provide from about 1.4 to about 3 equivalents of acid, relative to cyanohydrin, with a catalyst comprising supported zerovalent palladium in the presence of hydrogen at a pressure from 10 up to about 2,000 pounds per square inch and a temperature from about 10° to 85° C. for a time sufficient to effect the hydrogenation of the nitrile moiety of the cyanohydrin to an imine, separating the aqueous solution of the imine from hydrogen, hydrolyzing the imine to the corresponding aldehyde, and recovering the aldehyde.

2. The process of claim 1 where the cyanohydrin is the HCN adduct of erythrose or threose.

3. The process of claim 1 where the cyanohydrin is the HCN adduct of ribose, arabinose, xylose or lyxose.

4. The process of claim 1 where the cyanohydrin is the HCN adduct of allose, altrose, glucose, mannose, gulose, idose, galactose, or talose.

5. The process of claim 1 where the acid is selected from the group consisting of sulfuric, hydrochloric, phosphoric, and trifluoroacetic acid.

6. The process of claim 5 where the acid is sulfuric acid.

7. The process of claim 1 where palladium is dispersed on a porous solid organic polymeric resin having a surface area of at least 30 $m^2/g$.

8. The process of claim 7 where the resin is selected from the group consisting of polystyrenes, polyacrylamides, and poly(vinyl pyridine).

9. The process of claim 8 where the resin is a polystyrene.

10. The process of claim 9 where the resin is a polystyrene having pendant perfluoroalkyl carboxylic acid moieties.

11. The process of claim 8 where the resin is a polyacrylamide.

12. The process of claim 8 where the resin is a poly(vinyl pyridine).

13. The process of claim 7 where the resin has a surface area greater than about 50 $m^2/g$.

14. The process of claim 13 where the resin has a surface area greater than about 100 $m^2/g$.

15. The process of claim 1 where the hydrogen pressure is between about 100 and about 1,500 pounds per square inch.

16. The process of claim 15 where the hydrogen pressure is from about 600 to about 1,000 pounds per square inch.

17. The process of claim 1 where contacting is performed with a fixed mass of the catalyst.

* * * * *